United States Patent [19]
Lee et al.

[11] Patent Number: 5,665,880
[45] Date of Patent: Sep. 9, 1997

[54] METHOD OF PREPARATION OF PHYSOSTIGMINE CARBAMATE DERIVATIVES FROM ESERETHOLES

[75] Inventors: Thomas B. K. Lee, Whitehouse Station; Zhongli Gao, Somerville, both of N.J.

[73] Assignee: Hoechst Marion Roussel, Inc., Cincinnati, Ohio

[21] Appl. No.: 739,402

[22] Filed: Oct. 31, 1996

[51] Int. Cl.$^6$ .................................................. C07D 471/02
[52] U.S. Cl. ............................................. 546/147; 548/429
[58] Field of Search ................................ 546/147; 548/429

[56] References Cited

U.S. PATENT DOCUMENTS

| | | | |
|---|---|---|---|
| 4,791,107 | 12/1988 | Hamer et al. | 514/228.2 |
| 4,831,155 | 5/1989 | Brufani et al. | 548/421 |
| 4,914,102 | 4/1990 | Glamkowski | 514/232.8 |
| 4,937,341 | 6/1990 | Glamkowski | 544/142 |
| 4,971,992 | 11/1990 | Glamkowski et al. | 514/411 |
| 4,983,616 | 1/1991 | O'Malley et al. | 514/339 |
| 5,077,289 | 12/1991 | Glamkowski et al. | 514/211 |
| 5,081,117 | 1/1992 | Glamkowski et al. | 514/216 |
| 5,091,541 | 2/1992 | O'Malley et al. | 548/429 |
| 5,153,193 | 10/1992 | Flanagan et al. | 514/411 |
| 5,173,497 | 12/1992 | Flanagan | 514/411 |
| 5,177,101 | 1/1993 | Glamkowski et al. | 514/411 |
| 5,187,165 | 2/1993 | Hamer et al. | 514/307 |
| 5,216,017 | 6/1993 | Allen et al. | 514/411 |
| 5,231,093 | 7/1993 | Flanagan et al. | 548/486 |
| 5,234,941 | 8/1993 | Flanagan et al. | 514/411 |
| 5,260,452 | 11/1993 | Glamkowski et al. | 548/486 |
| 5,264,587 | 11/1993 | Flanagan | 548/429 |
| 5,274,117 | 12/1993 | Lee et al. | 548/429 |
| 5,302,721 | 4/1994 | Wong et al. | 548/429 |
| 5,350,762 | 9/1994 | Martin et al. | 514/411 |
| 5,387,695 | 2/1995 | Lee et al. | 548/486 |
| 5,455,354 | 10/1995 | Wong et al. | 546/147 |
| 5,498,726 | 3/1996 | Lee et al. | 548/429 |
| 5,541,216 | 7/1996 | Hamer et al. | 514/411 |
| 5,541,340 | 7/1996 | Hamer et al. | 548/429 |
| 5,547,977 | 8/1996 | Hamer et al. | 514/41.1 |
| 5,550,254 | 8/1996 | Hamer et al. | 548/429 |
| 5,591,864 | 1/1997 | Glamkowski et al. | 548/429 |

FOREIGN PATENT DOCUMENTS

| | | |
|---|---|---|
| 0253372 | 1/1988 | European Pat. Off. |
| 2905054 | 8/1980 | Germany. |
| 9200072 | 1/1992 | WIPO. |

OTHER PUBLICATIONS

Fieser & Fieser, Reagents for Organic Synthesis, pp. 451–452.
Organic Syntheses, Collective vol. 3, pp. 753–756 (1955).
Dakin, Am. chem. J. 42, 447 pp. 150–153 (1909).

*Primary Examiner*—Zinna Northington Davis
*Attorney, Agent, or Firm*—William R. Boudreaux

[57] ABSTRACT

This invention relates to a process for the preparation of a product of the formula

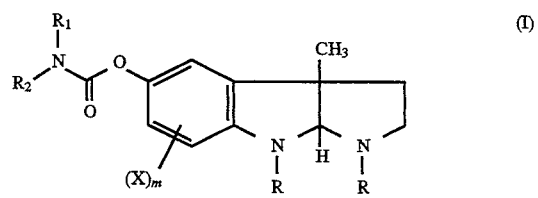

wherein R is loweralkyl; $R_1$, is hydrogen, loweralkyl, lowercycloalkyl, lowercycloalkylloweralkyl, lowerbicycloalkyl, aryl or arylloweralyl; $R_2$ is lower alkyl, lowercycloalkyl, lowercycloalkylloweralkyl, lowerbicycloalkyl, aryl or arylloweralkyl; or $R_1$ and $R_2$ taken together with the nitrogen atom to which they are attached form a group of the formula (Ia)

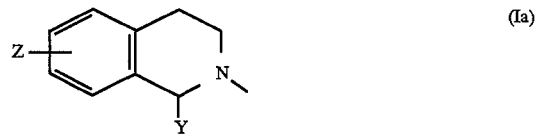

wherein Y is hydrogen or loweralkyl and Z is hydrogen, loweralkyl, halogen, loweralkoxy or hydroxy; X is loweralkyl, loweralkoxy, halogen or trifluoromethyl; and m is 0, 1 or 2; or a pharmaceutically acceptable salt thereof; which process comprises(a) contacting a compound of formula (II) as defined herein with fortified hydrogen bromide to afford a compound of formula (III) as defined herein; contacting the reaction mixture containing a compound of formula (III) with either (1) an isocyanate of formula $R_1NCO$ or (2) with a compound of formula (IV) as defined to afford a compound of formula (V) as defined herein and contacting the reaction mixture containing the compound of formula (V) with an amine of the formula $R_1R_2NH$ herein in the presence of a carboxylic acid of the formula $R_5COOH$ and forming and isolating the product of Formula (I).

10 Claims, No Drawings

METHOD OF PREPARATION OF PHYSOSTIGMINE CARBAMATE DERIVATIVES FROM ESERETHOLES

This application relates to a novel process for the preparation of a product of the formula

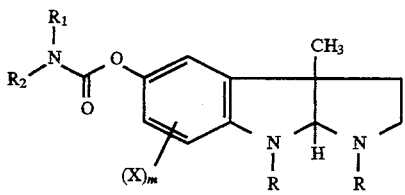

wherein

R is loweralkyl;

$R_1$ is hydrogen, loweralkyl, lowercycloalkyl, lowercycloalkylloweralkyl, lowerbicycloalkyl, aryl or arylloweralkyl;

$R_2$ is loweralkyl, lowercycloalkyl, lowercycloalkylloweralkyl, lowerbicycloalkyl, aryl or arylloweralkyl; or $R_1$ and $R_2$ taken together with the nitrogen atom to which they are attached form a group of the formula (Ia)

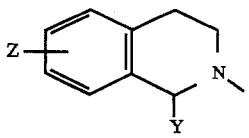

wherein Y is hydrogen or loweralkyl and Z is hydrogen, loweralkyl, halogen, loweralkoxy or hydroxy;

X is loweralkyl, loweralkoxy, halogen or trifluoromethyl; and m is 0, 1 or 2;

or a pharmaceutically acceptable salt thereof; which process comprises (a) contacting a compound of formula (II)

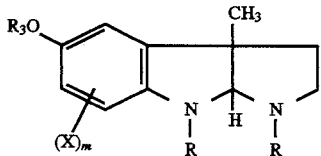

wherein R, X and m are as defined above and $R_3$ is loweralkyl, with fortified hydrogen bromide to afford a compound of formula (III)

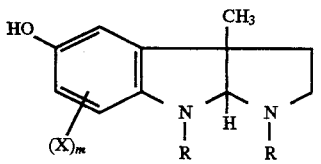

wherein R, X and m are as defined above;

(b) contacting the reaction mixture containing the compound of Formula (III) either (1) with an isocyanate of the formula $R_1NCO$ and isolating a product of formula (I) wherein $R_2$ is hydrogen; or (2) with a compound of formula (IV)

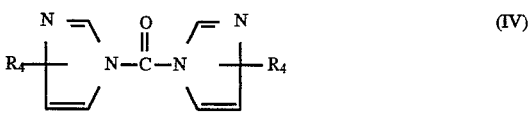

wherein $R_4$ is hydrogen or loweralkyl to afford a compound of formula (V)

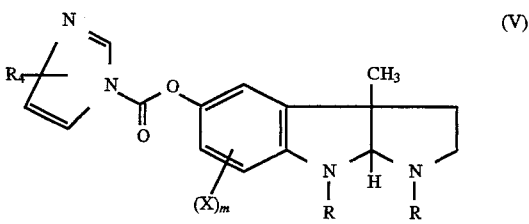

wherein R, $R_4$, X and m are as above;

(c) contacting the reaction mixture containing the compound of formula (V) obtained in step (b) with a compound of the formula $$R_1R_2NH$$

wherein $R_1$ and $R_2$ are as above in the presence of a carboxylic acid of the formula $$R_5COOH$$

wherein $R_5$ is loweralkyl; and forming and isolating the product of formula (I).

This application further provides a novel process for the preparation of a product of formula (III)

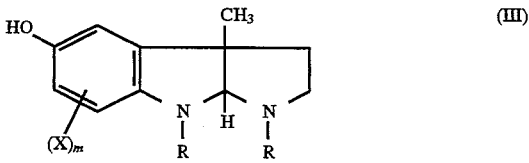

wherein R is loweralkyl; X is loweralkyl, loweralkoxy, halogen or trifluoromethyl; and m is 0, 1 or 2; or a pharmaceutically acceptable salt thereof; comprising contacting a compound of formula (II)

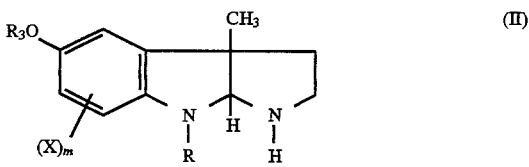

wherein R, X and m are as defined above and $R_3$ is loweralkyl, with fortified hydrogen bromide to afford a compound of formula (III).

The compounds of formula (I) are useful as memory-enhancing and analgesic agents as disclosed in U.S. Pat. No. 4,791,107, issued Dec. 13, 1988; U.S. Pat. No. 5,187,165, issued Feb. 19, 1993; U.S. Pat. No. 5,541,216, issued Jul. 30, 1996; and U.S. Pat. No. 5,547,977, issued Aug. 20, 1996. The compounds of formula (III) are useful as memory-enhancing and analgesic agents as disclosed in U.S. Pat. No. 5,541,216, issued Jul. 30, 1996; Canadian Pat. No. 1,137, 489, issued Dec. 14, 1982; and as useful intermediates for making additional memory-enhancing and analgesic agents.

Unless otherwise stated or indicated, the term loweralkyl means a straight or branched alkyl group having from 1 to 6 carbon atoms. Examples of alkyl include methyl, ethyl, n-propyl, isobutyl, pentyl, hexyl, and the like.

Unless otherwise stated or indicated, the term cycloalkyl means a saturated ring containing 3 to 7 carbon atoms. Examples of cycloalkyl include cyclopropyl, cyclohexyl, cycloheptyl, and the like.

Unless otherwise stated or indicated, the term bicycloalkyl means a group having from 7 to 11 carbons.

Unless otherwise stated or indicated, the term halogen means fluorine, chlorine, bromine or iodine.

Unless otherwise stated or indicated, the term aryl means an unsubstituted phenyl or aromatic heterocyclic group; or a phenyl or aromatic heterocyclic group substituted with 1,2 or 3 substituents each of which being independently loweralkyl, loweralkoxy, halogen, hydroxy, trifluoromethyl, phenoxy or benzyloxy.

The term "pharmaceutically acceptable salts" refers to acid addition salts. The expression "pharmaceutically acceptable acid addition salts" is intended to apply to any non-toxic organic or inorganic acid addition salt of the compounds of formula (I). Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are, for example, acetic, glycolic, lactic, pyruvic, malonic, succinic, glutaric, fumaric, malic, tartaric, citric, ascorbic, maleic, hyroxymaleic, benzoic, hydroxybenzoic, phenylacetic, cinnamic, salicylic, 2-phenoxybenzoic, and sulfonic acids such as p-toluenesulfonic acid, methanesulfonic acid and 2-hydroxyethanesulfonic acid. Such salts can exist in either a hydrate or substantially anhydrous form.

Other methods for preparation of physostigmine carbamate derivatives are known. See, for example, Hamer et al., U.S. Pat. No. 3,791,107; Brufani et al., U.S. Pat. No. 4,831,155; Wong et al., U.S. Pat. No. 5,302,721; and Wong et al., U.S. Pat. No. 5,455,354. There remains a need, however, for processes providing higher yields, ecologically allowed reagents and/or less costly means for obtaining these compounds.

The process of this invention has the following major advantages over the previously known methods:

Fortified hydrobromic acid is used as a dealkylating agent as well as the reaction solvent. This reagent is less expensive than other previously used dealkylating agents such as boron tribromide or aluminum chloride.

No halogenated solvents are employed. Halogenated solvents such as dichloromethane or dichloroethane are environmentally undesirable.

No preparative column chromatography purification is required. Preparative column chromatography is expensive, labor-intensive and limiting in scale-up throughput.

Environmental emission control is more effective as the hydrobromic acid can be recycled.

The compounds of this invention are prepared by utilizing the synthetic steps described below. Throughout the description of the synthetic steps, the substituents "X", "m", "R", "$R_1$", "$R_2$", "$R_3$", "$R_4$" and "$R_5$" shall have the respective meanings given above unless otherwise indicated.

In structural formulae depicting the compounds of this invention, heavy lines (—◂) coming out of the 3a-carbon and 8a-carbon of the 1,2,3,3a,8,8a-hexahydropyrrolo[2,3-b] indole ring system signify that the two substituents are above the average plane of the three-ring system, whereas dotted lines (--◂) signify that the two substituents are below the average plane of the three-ring system, and wavy lines (∼∼∼) signify that the two substituents are both above said plane or below said plane. Because of conformational constraints, the two substituents at the 3a- and 8a-positions must be both above said average plane or both below said average plane. Thus, in formula (I), the substituents at the 3a- and 8a-positions are cis since they are on the same side of the three ring system. Where said substituents are both above the average plane of the three ring system, the configuration will be referred to as 3aS-cis and where both substituents are below the average plane of the ring, the configuration will be referred to as 3aR-cis. These two types of configurations are depicted below.

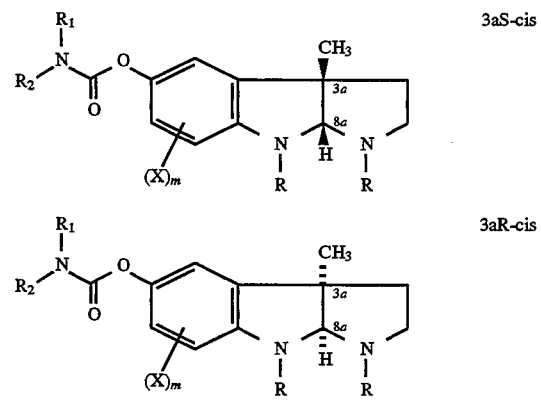

Both of said cis isomers, namely, the 3aS-cis isomer and the 3aR-cis isomer are encompassed by each given compound name or structural formula containing wavy lines mentioned above. Furthermore, all mixtures of the 3aS-cis and 3aR-cis isomers including the racemic mixture (1:1 ratio of 3aS-cis:3aR-cis) are encompassed.

SCHEME

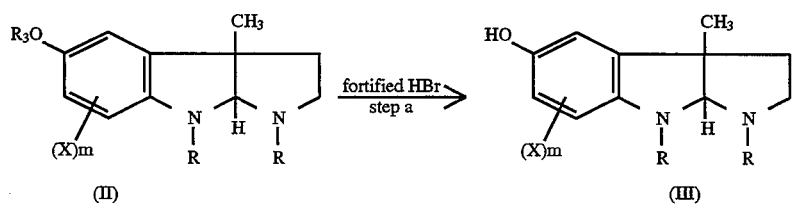

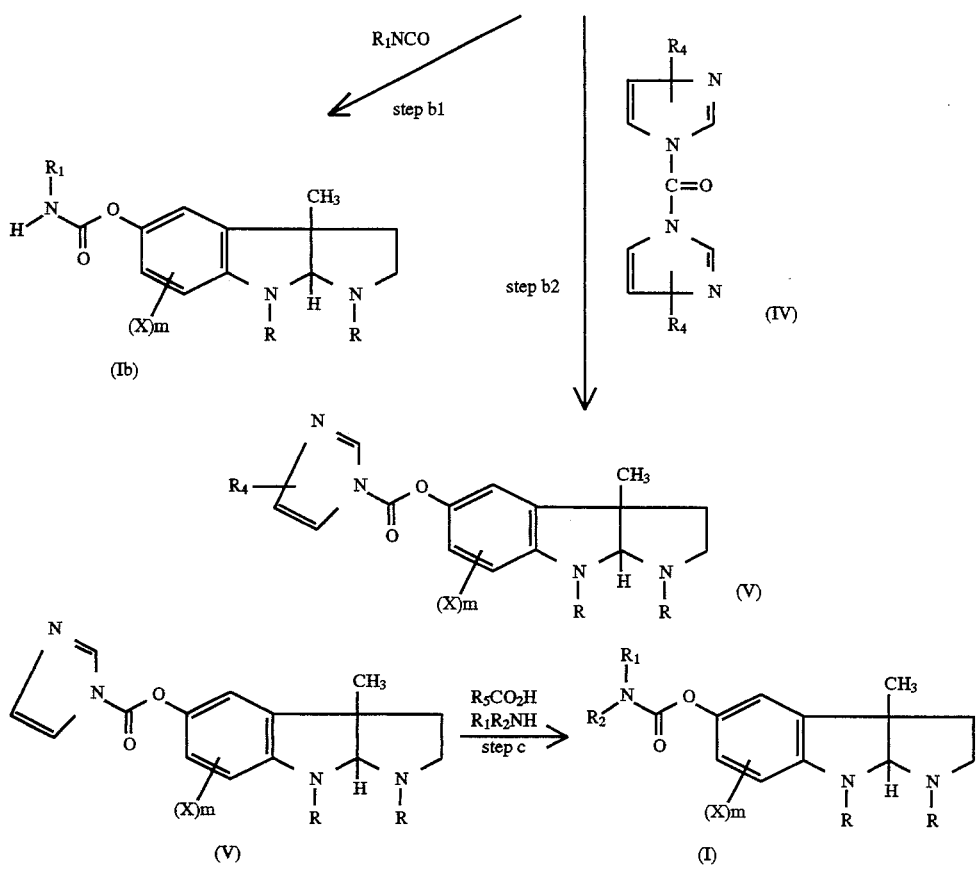

In step a, the compound of formula (II) is contacted with fortified hydrogen bromide at room temperature. The reaction is then heated to a temperature ranging from 80° C.–100° C., preferably 90°–95° C., for a period of time ranging from 1 to 5 hours, preferably 3 to 4 hours. The reaction is then cooled, rinsed with water and neutralized with a suitable base, for example, 20% potassium hydroxide. The appropriate compound of formula (III) is then extracted into an organic solvent such as butyl acetate or ethyl acetate and the resulting solution is dried with a drying agent such as potassium carbonate or molecular sieves.

In this application, the term "fortified hydrogen bromide" is meant to encompass concentrations of hydrogen bromide of from about 55% to about 62%. Preferably, the hydrogen bromide concentration is within the range of from about 57% to about 60%. Fortified hydrogen bromide is obtained from 48% hydrogen bromide using techniques and procedures well known by those of ordinary skill in the art. Additionally, 62% hydrogen bromide may be obtained commercially.

In step b1, the compound of formula (III) is contacted with either an alkyl isocyanate or a substituted alkyl isocyanate to form a compound of Formula (I) where $R_2$ is hydrogen, as represented by structure (Ib) above. In this instance, the reaction temperature is generally between about 0° C. and about 25° C., preferably about 5° C. to about 10° C. The reaction is monitored and the pH is maintained between about 9 and 10 by the addition of a base such as, for example, potassium t-butoxide or an acid such as, for example, acetic aid.

In step b2, the compound of Formula (III) is contacted with the carbonyldiimidazole compound of Formula (IV) to provide the imidazole carbamate product of structure (V). In this instance, the addition is carried out at about 0° C. to about 25° C., preferably about 20° C.

In step c, the reaction is typically conducted by adding sequentially a carboxylic acid, such as, for example, acetic acid, and an amine such as tetrahydroisoquinoline to the solution obtained above. The pH of the acidic solution may optionally be acidified to a pH of from about 4.5 to about 6 with an acid, such as acetic acid, prior to contact with the appropriate amine. The addition of the amine is generally carried out from about −15° C. to about 25° C., preferably at from about −10° C. to about 20° C.

Examples of compounds made by the process of this invention include those listed below as well as the 3aR-cis isomers thereof and mixtures of the 3aS-cis and 3aR-cis isomers including the racemic mixtures:

(3aS-cis)-1,2,3,3a,8,8a-hexahydro-1,3a,8-trimethylpyrrolo[2,3-b]indol-5-ol, (1,2,3,4-tetrahydroisoquinolinyl)carbamate;

(3aS-cis)-1,2,3,3a,8,8a-hexahydro-1,3a,8-trimethylpyrrolo[2,3-b]indol-5-ol, (1-methyl-1,2,3,4-tetrahydroisoquinolinyl)carbamate;

(3aS-cis)-1,2,3,3a,8,8a-hexahydro-1,3a,8-trimethylpyrrolo[2,3-b]indol-5-ol, (1ethyl-1,2,3,4-tetrahydroisoquinolinyl)carbamate;

(3aS-cis)-1,2,3,3a,8,8a-hexahydro-1,3a,8-trimethylpyrrolo[2,3-b]indol-5-ol, (1-propyl-1,2,3,4-tetrahydroisoquinolinyl)carbamate;

(3aS-cis)-1,2,3,3a,8,8a-hexahydro-1,3a,8-trimethylpyrrolo[2,3-b]indol-5-ol, (1-butyl-1,2,3,4-tetrahydroisoquinolinyl)carbamate;

(3aS-cis)-1,2,3,3a,8,8a-hexahydro-1,3a,8-trimethylpyrrolo[2,3-b]indol-5-ol, (6-chloro-1,2,3,4-tetrahydroisoquinolinyl)carbamate;

(3aS-cis)-1,2,3,3a,8,8a-hexahydro-1,3a,8trimethylpyrrolo[2,3-b]indol-5-ol, (7-chloro-1,2,3,4-tetrahydroisoquinolinyl)carbamate;

(3aS-cis)-1,2,3,3a,8,8a-hexahydro-1,3a,8-trimethylpyrrolo[2,3-b]indol-5-ol, (6-chloro-1-methyl-1,2,3,4-tetrahydroisoquinolinyl)carbamate;

(3aS-cis)-1,2,3,3a,8,8a-hexahydro-1,3a,8-trimethylpyrrolo[2,3-b]indol-5-ol, (7-chloro-1-methyl-1,2,3,4-tetrahydroisoquinolinyl)carbamate;

(3aS-cis)-1,2,3,3a,8,8a-hexahydro-1,3a,8-trimethylpyrrolo[2,3-b]indol-5-ol, (6-hydroxy-1,2,3,4-tetrahydroisoquinolinyl)carbamate;

(3aS-cis)-1,2,3,3a,8,8a-hexahydro-1,3a,8-trimethylpyrrolo[2,3-b]indol-5-ol, (7-hydroxy-1,2,3,4-tetrahydroisoquinolinyl)carbamate;

(3aS-cis)-1,2,3,3a,8,8a-hexahydro-1,3a,8-trimethylpyrrolo[2,3-b]indol-5-ol, (6-hydroxy-1-methyl-1,2,3,4-tetrahydroisoquinolinyl)carbamate;

(3aS-cis)-1,2,3,3a,8,8a-hexahydro-1,3a,8-trimethylpyrrolo[2,3-b]indol-5-ol, (7-hydroxy-1-methyl-1,2,3,4-tetrahydroisoquinolinyl)carbamate;

(3aS-cis)-1,2,3,3a,8,8a-hexahydro-1,3a,8-trimethylpyrrolo[2,3-b]indol-5-ol, cyclohexyl carbamate ester;

(3aS-cis)-1,2,3,3a,8,8a-hexahydro-1,3a,8-trimethylpyrrolo[2,3-b]indol-5-ol, 3-chlorophenyl carbamate ester fumarate;

(3aS-cis)-1,2,3,3a,8,8a-hexahydro-1,3a,8-trimethylpyrrolo[2,3-b]indol-5-ol, 3-chlorophenyl carbamate ester; and (3aS-cis)-1,2,3,3a,8,8a-hexahydro-1,3a,8-trimethylpyrrolo[2,3-b]indol-5-ol, 1-(phenyl)ethyl carbamate ester.

The following examples are presented in order to illustrate the invention and are not to be construed as limiting the invention in any way.

EXAMPLE 1

Preparation of (3aS-cis)-1,2,3,3a,8,8a-hexahydro-1,3a,8-trimethylpyrrolo[2,3-b]indol-5-ol, (1,2,3,4-tetrahydroisoquinolinyl)carbamate (HP-290) by using 48% HBr as dealkylation agent 20.0 g (81 mmol) of eserethole was dissolved in 80 mL of HBr (48%) at room temperature under nitrogen. The reaction was heated at 90°–95° C. for 3.5 h. The reaction mixture was poured into 250 mL of ice water, rinsed with 50 mL of water.

The solution was neutralized with 20% KOH and then extracted with butyl acetate (2×100 mL). The combined butyl acetate solution was dried over 40 g of potassium carbonate briefly at room temperature under nitrogen. The drying material was filtered. To the butyl acetate filtrate was added 1,1-carbonyldiimidazole (CDI), followed by 14.8 mL of acetic acid and 12.02 g (90 mmol) of 1,2,3,4-tetrahydroisoquinoline. The mixture was allowed to stir at an ambient temperature under nitrogen overnight. The crude reaction mixture contained 3.90 g (12.72%) of HP 290 as assayed by external standard HPLC. This reaction mixture was washed with 40 mL of water and the aqueous solution was extracted with butyl acetate (2×40 mL). The combined organic layers were extracted with dilute hydrochloric acid.

The aqueous solution was neutralized with sodium hydroxide and was extracted with cyclohexane (2×125 mL). The combined cyclohexane was dried with potassium carbonate and stirred with 25 g of alumina. The absorbent was filtered and the filtrate cake was rinsed with cyclohexane. This solution was concentrated to a syrup which contained 2.66 g (8.67%) of HP 290. Attempt of crystallization of this syrup from cyclohexane failed to give crystalline product HP 290.

EXAMPLE 2

Preparation of (3aS-cis)-1,2,3,3a,8,8a-hexahydro-1,3a,8-trimethylpyrrolo[2,3-b]indol-5-ol, (1,2,3,4-tetrahydroisoquinolinyl)carbamate (HP 290) by using 62% HBr as dealkylation agent a) Preparation of Fortified (60–62%) Hydrogen Bromide 1.0 L of commercially available aq. HBr (48%) was bubbled through gaseous hydrogen bromide at 0° C.—room temperature until the concentration of Hbr reached 60–62% as assayed by titration. 80 mL or this solution was used in the following step.

b) Preparation of (3aS-cis)-1,2,3,3a,8,8a-hexahydro-1,3a,8-trimethylpyrrolo[2,3-b]indol-5-ol, (1,2,3,4-tetrahydroisoquinolinyl)carbamate 20.00 g (81 mmol) of eserethole was dissolved in 80 mL of HBr (62%) at room temperature under nitrogen. The reaction was heated at 90°–95° C. for 3.5 h. The reaction mixture was poured into 250 mL of ice water, rinsed with 50 mL of water. The solution was neutralized with 20% KOH and then extracted with butyl acetate (2×100 mL). The combined butyl acetate solution was dried over 40 g of potassium carbonate briefly at r.t. under nitrogen. The drying material was filtered. To the butyl acetate solution was added 1,1-carbonyldiimidazole (CDI), followed by 14.8 mL of acetic acid and 12.02 g (90 mmol) of 1,2,3,4-tetrahydroisoquinoline. The mixture contained 26.23 g (85.58%) of HP 290 as assayed by external standard HPLC. This reaction mixture was washed with 40 mL of water and the aqueous solution was extracted with butyl acetate (2×40 mL). The combined organic layers were extracted dilute hydrochloric acid. The aqueous solution was neutralized with sodium hydroxide and was extracted with cyclohexane (2×125 mL). The combined cyclohexane was dried with potassium carbonate and stirred with 25 g of alumina. The absorbent was filtered and the filtrate cake was rinsed with cyclohexane. This solution was concentrated to a syrup which contained 27.07 g (75.27%) of HP 290. Crystallization of this syrup from cyclohexane provided 22.07 g (72.01%) of HP 290 as a white crystalline product.

EXAMPLE 3

Preparation of (3aS-cis)-1,2,3,3a,8,8a-hexahydro-1,3a,8-trimethylpyrrolo[2,3-b]indol-5-ol, cyclohexyl carbamate ester To a solution of (–)-eseroline (2.2 g, the "butyl acetate solution" from Example 2), there is added benzene (50 mL) containing cyclohexyl isocyanate (1.2 g) and the mixture is stirred at 25° C. for 3 hours. The product is isolated by extraction of the butyl acetate solution with water (200 mL) followed by sodium hydroxide solution (100 mL, 0.5N) and water (100 mL). The residue is dried over anhydrous sodium sulfate and the butyl acetate solution is concentrated under reduced pressure to yield the title compound.

EXAMPLE 4

Preparation of (3aS-cis)-1,2,3,3a,8,8a-hexahydro-1,3a,8-trimethylpyrrolo[2,3-b]indol-5-ol, 3-chlorophenyl carbamate ester fumarate To a solution of (–)-eseroline (2.2 g, the "butyl acetate solution" from Example 2), there is added 3-chlorophenyl isocyanate (1.5 g) over 1 hour at 5° C. and the mixture is stirred at 25° C. for 3 hours. The product is isolated as the fumarate salt following water washing, concentration under reduced pressure, chromatographic purification on silica gel and acidification of the purified free base with fumaric acid (1 equiv.).

EXAMPLE 5

Preparation of (3aS-cis)-1,2,3,3a,8,8a-hexahydro-1, 3a,8-trimethylpyrrolo[2,3-b]indol-5-ol, 3-chlorophenyl carbamate ester To a solution of (−)-eseroline (2.2 g, the "butyl acetate solution" from Example 2), there is added 3-chlorophenyl isocyanate (1.6 g) at −5° C. over 5 minutes. After stirring for 0.25 hours, the title compound is isolated substantially as described in Example 2.

EXAMPLE 6

Preparation of (3aS-cis)-1,2,3,3a, 8,8a-hexahydro-1, 3a,8-trimethylpyrrolo[2,3-b]indol-5-ol, 1-(phenyl) ethyl carbamate ester To a solution of (−)-eseroline (2.2 g, the "butyl acetate solution" from Example 2), there is added (S)-(−)-α-methylbenzyl isocyanate (1.5 g) over 1.5 hours at 10° C. The title compound is isolated substantially as described in Example 2.

EXAMPLE 7

Preparation of(3aS-cis)-1,2,3,3a,8,8a-hexahydro-1, 3a,8-trimethylpyrrolo[2,3-b]indol-5-ol, (1,2,3,4-tetrahydroisoquinolinyl)carbamate (HP 290) by using 57% HBr as dealkylation agent a) Preparation of Fortified (57%) Hydrogen Bromide To 700 mL of commercially available aq. HBr (48%) was bubbled through gaseous hydrogen bromide at 0° C.—room temperature until the concentration of HBr reached 57% as assayed by titration.

b) Preparation of (3aS-cis)-1,2,3,3a,8,8a-hexahydro-1,3a,8-trimethylpyrrolo[2,3-b]indol-5-ol, (1,2,3,4-tetrahydroisoquinolinyl)carbamate To the solution in Example 7, step a, was added 100 g (0.41 mol) of eserethole at room temperature under nitrogen. The mixture was heated under nitrogen with stirring for 5–6 hours. The mixture was distilled to remove excess of HBr (recyclable) and the residue was dissolved in 1.0 L of water. One fifth of this solution was basified with 50% aq NaOH (16.5 g) and extracted with ethyl acetate. The extract containing eseroline was dried over potassium carbonate, treated briefly with 15.1 g (94 mmol) of 1,1-carbonyldiimidazole (CDI) followed by 14.8 mL of acetic acid and 12.0 g (90 mmol) of 1,2,3,4-tetrahydroisoquinoline. The mixture was allowed to stir at an ambient temperature overnight. The reddish reaction mixture was washed with water. The aqueous solution was back extracted with ethyl acetate. The ethyl acetate extracts were washed with dilute sodium hydroxide, followed by water and dried over potassium carbonate. Removal of the solvent in vacuo gave a syrup which was dissolved in 200 mL of cyclohexane and slurried with 25 g of alumina for 30 rain and filtered. The filtrate cake was rinsed with cyclohexane and the filtrate was concentrated and the residue was crystallized from cyclohexane to afford 21.43 g (70%) of the product as a white crystalline solid.

TABLE 1

Reaction profile of dealkylation of eserethole with 48% HBr and 62% Hbr

| | 48% HBr* | | 62% HBr* | |
|---|---|---|---|---|
| Time | Eseroline (%) | Eserethole (%) | Eseroline (%) | Eserethole (%) |
| 0:30 | 1.58 | 98.42 | 51.73 | 48.22 |
| 1:00 | 2.73 | 96.82 | 60.13 | 38.11 |
| 1:30 | 4.11 | 95.35 | 76.11 | 21.46 |
| 3:45 | 5.45 | 93.92 | 84.14 | 12.70 |
| 2:30 | 6.56 | 92.48 | 88.09 | 7.42 |
| 3:00 | 8.70 | 89.93 | 90.92 | 2.66 |
| 3:30 | 9.91 | 88.76 | 91.80 | 1.05 |

*Conversion of eserethole to eseroline in the reaction mixture as determined by HPLC (relative ratio)

TABLE 2

Comparison of the yield of HP 290 with 48% HBr and 62% HBr

| | 48% HBr | | 62% HBr | |
|---|---|---|---|---|
| Sample | HP 290 yield (%) | Eserethole yield (%) | HP 290 yield (%) | Eserethole yield (%) |
| Crude reaction mixture* | 12.72 | 75.71 | 85.58 | 0 |
| Crystalline product | 0 | — | 72 | — |

*Quantitative assay of HP 290 and eserethole by external standard HPLC.

Advantages of 62% HBr vs. 48% HBr:

The dealkylation with 48% HBr is too slow to be a practical method of dealkylation of eserethole. The dealkylation with 62% HBr is fast and offers a convenient and practical dealkylation methodology for eserethole.

Dealkylation of eserethole with 48% HBr provides only ~13% yield of crude HP 290; while dealkylation of eserethole with 62% HBr provides ~86% yield of crude HP 290 under exactly the same conditions for both reagents.

The crude HP 290 product from the 48% HBr dealkylation was too impure to effect successful crystallization of HP 290 from cyclohexane, whereas the crude HP 290 from 62% HBr dealkylation gave 72% of crystalline HP 290 from cyclohexane.

What is claimed is:

1. A process for the preparation of a compound of the formula

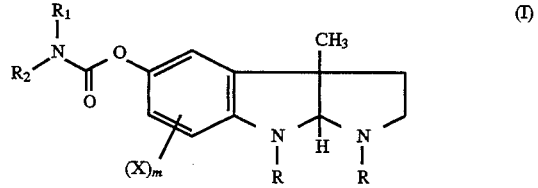

wherein

R is loweralkyl;

$R_1$ is hydrogen, loweralkyl, lowercycloalkyl, lowercycloalkylloweralkyl, lowerbicycloalkyl, aryl or arylloweralkyl;

$R_2$ is loweralkyl, lowercycloalkyl, lowercycloalkylloweralkyl, lowerbicycloalkyl, aryl or arylloweralkyl; or $R_1$ and $R_2$ taken together with the nitrogen atom to which they are attached form a group of the formula (Ia)

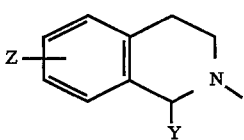

wherein Y is hydrogen or loweralkyl and Z is hydrogen, loweralkyl, halogen, loweralkoxy or hydroxy;

X is loweralkyl, loweralkoxy, halogen or trifluoromethyl; and m is 0, 1 or 2;

or a pharmaceutically acceptable salt thereof; which process comprises (a) contacting a compound of formula (II)

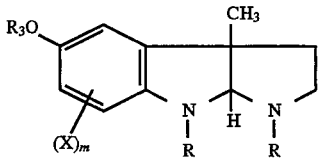

wherein R, X and m are as defined above and $R_3$ is loweralkyl, with fortified hydrogen bromide to afford a compound of formula (III)

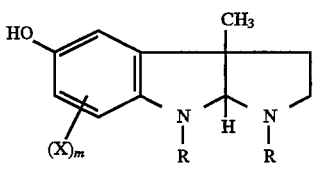

wherein R, X and m are as defined above;

(b) contacting the reaction mixture containing the compound of Formula (III) either (1) with an isocyanate of the formula $R_1NCO$ and isolating a product of formula (I) wherein $R_2$ is hydrogen; or (2) with a compound of formula (IV)

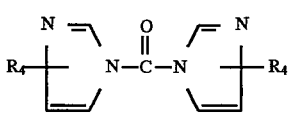

wherein $R_4$ is hydrogen or loweralkyl to afford a compound of formula (V)

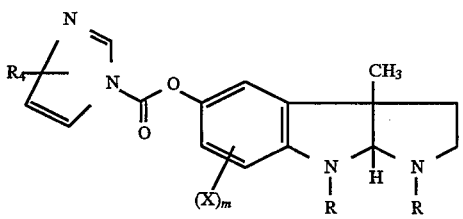

wherein R, $R_4$, X and m are as above;

(c) contacting the reaction mixture containing the compound of formula (V) obtained in step (b) with a compound of the formula

$R_1R_2NH$ wherein $R_1$ and $R_2$ are as above in the presence of a carboxylic acid of the formula

$R_5COOH$ wherein $R_5$ is loweralkyl; and forming and isolating the product of formula (I).

2. A process according to claim 1 wherein said fortified hydrogen bromide is hydrogen bromide with a concentration within the range of from about 60% to about 62%.

3. A process according to claim 1 wherein said fortified hydrogen bromide is hydrogen bromide with a concentration within the range of from about 57% to about 60%.

4. A process according to claim 1 wherein R and $R_3$ are loweralkyl and X is hydrogen.

5. A process according to claim 4 wherein R is methyl and $R_3$ is ethyl.

6. A process according to claim 5 wherein the compound of formula (II) is (−)-eserethole.

7. A process according to claim 1 wherein R is loweralkyl, X is hydrogen and $R_1$ and $R_2$ together with the nitrogen to which they are attached form 1,2,3,4-tetrahydroisoquinoline group or a 1-methyl-1,2,3,4-tetrahydroisoquinoline group.

8. A process according to claim 7 wherein R is methyl.

9. A process according to claim 1 wherein the compound of formula (I) is selected from the group consisting of (3aS-cis)-1,2,3,3a,8,8a-hexahydro-1,3a,8-trimethylpyrrolo[2,3-b]indol-5-ol, (1,2,3,4-tetrahydroisoquinolinyl)carbamate;

(3aS-cis)-1,2,3,3a,8,8a-hexahydro-1,3a,8-trimethylpyrrolo[2,3-b]indol-5-ol, (1-methyl-1,2,3,4-tetrahydroisoquinolinyl)carbamate;

(3aS-cis)-1,2,3,3a,8,8a-hexahydro-1,3a,8-trimethylpyrrolo[2,3-b]indol5-ol, (1-ethyl-1,2,3,4-tetrahydroisoquinolinyl)carbamate;

(3aS-cis)-1,2,3,3a,8,8a-hexahydro-1,3a,8-trimethylpyrrolo[2,3-b]indol-5-ol, (1-propyl-1,2,3,4-tetrahydroisoquinolinyl)carbamate;

(3aS-cis)-1,2,3,3a,8,8a-hexahydro-1,3a,8-trimethylpyrrolo[2,3-b]indol-5-ol, (1-butyl-1,2,3,4-tetrahydroisotsoqluinolinyl)carbamate;

(3aS-cis)-1,2,3,3a,8,8a-hexahydro-1,3a,8-trimethylpyrrolo[2,3-b]indol-5-ol, (6-chloro-1,2,3,4-tetrahydroisoquinolinyl)carbamate;

(3aS-cis)-1,2,3,3a,8,8a-hexahydro-1,3a,8-trimethylpyrrolo[2,3-b]indol-5-ol, (7-chloro-1,2,3,4-tetrahydroisoquinolinyl)carbamate;

(3aS-cis)-1,2,3,3a,8,8a-hexahydro-1,3a,8-trimethylpyrrolo[2,3-b]indol-5-ol, (6-chloro-1-methyl-1,2,3,4-tetrahydroisoquinolinyl)carbamate;

(3aS-cis)-1,2,3,3a,8,8a-hexahydro-1,3a,8-trimethylpyrrolo[2,3-b]indol-5-ol, (7-chloro-1-methyl-1,2,3,4-tetrahydroisoquinolinyl)carbamate;

(3aS-cis)-1,2,3,3a,8,8a-hexahydro-1,3a,8-trimethylpyrrolo[2,3-b]indol-5-ol, (6-hydroxy-1,2,3,4-tetrahydroisoquinolinyl)carbamate;

(3aS-cis)-1,2,3,3a,8,8a-hexahydro-1,3a,8-trimethylpyrrolo[2,3-b]indol-5-ol, (7-hydroxy-1,2,3,4-tetrahydroisoquinolinyl)carbamate;

(3aS-cis)-1,2,3,3a,8,8a-hexahydro-1,3a,8-trimethylpyrrolo[2,3-b]indol-5-ol, (6-hydroxy-1-methyl-1,2,3,4-tetrahydroisoquinolinyl)carbamate; and (3aS-cis)-1,2,3,3a,8,8a-hexahydro-1,3a,8-trimethylpyrrolo[2,3-b]indol-5-ol, (7-hydroxy-1-methyl-1,2,3,4-tetrahydroisoquinolinyl)carbamate.

10. A process according to claim 1 wherein said compound of formula (1) is (3aS-cis)-1,2,3,3a,8,8a-hexahydro-1,3a,8-trimethylpyrrolo[2,3-b]indol-5-ol, (1,2,3,4-tetrahydroisoquinolinyl)carbamate.

* * * * *